US006602215B1

(12) United States Patent
Richie, Jr.

(10) Patent No.: US 6,602,215 B1
(45) Date of Patent: Aug. 5, 2003

(54) ANKLE BRACE WITH ARCH SLING SUPPORT

(76) Inventor: Douglas H. Richie, Jr., 1460 La Perla Ave., Long Beach, CA (US) 90815

( * ) Notice: Subject to any disclaimer, the term of this patent is extended or adjusted under 35 U.S.C. 154(b) by 0 days.

(21) Appl. No.: 10/189,217

(22) Filed: Jul. 3, 2002

(51) Int. Cl.⁷ ................................................. A61F 5/00
(52) U.S. Cl. ........................................ 602/27; 128/882
(58) Field of Search ..................... 602/27–29; 128/882

(56) References Cited

U.S. PATENT DOCUMENTS

| 4,102,337 | A | * | 7/1978 | Golia ........................... 602/28 |
| 4,166,460 | A | * | 9/1979 | Applegate ..................... 602/27 |
| 4,494,534 | A | | 1/1985 | Hutson |
| 4,523,394 | A | | 6/1985 | Lindh et al. |
| 4,587,962 | A | | 5/1986 | Greene et al. |
| 4,753,229 | A | | 6/1988 | Sutherland |
| 4,982,733 | A | * | 1/1991 | Broadhurst et al. ........... 602/27 |
| 5,016,623 | A | | 5/1991 | Krahenbuhl |
| 5,069,202 | A | * | 12/1991 | Prock ........................... 602/27 |
| 5,151,081 | A | * | 9/1992 | Williams ...................... 602/27 |
| 5,209,722 | A | * | 5/1993 | Miklaus et al. ................ 602/27 |
| 5,376,068 | A | * | 12/1994 | Grifka .......................... 602/27 |
| 5,393,303 | A | * | 2/1995 | Shiono ......................... 602/27 |
| 5,445,603 | A | * | 8/1995 | Wilkerson .................... 602/27 |
| 5,472,411 | A | * | 12/1995 | Montag et al. ................ 602/23 |
| 5,496,263 | A | | 3/1996 | Fuller, II et al. |
| 5,501,659 | A | * | 3/1996 | Morris et al. .................. 602/27 |
| 5,603,692 | A | * | 2/1997 | Maxwell ....................... 602/28 |
| 5,700,237 | A | * | 12/1997 | Hess ............................. 602/27 |
| 5,741,222 | A | | 4/1998 | Fiore |
| 5,860,423 | A | * | 1/1999 | Thompson ................... 128/882 |
| 5,887,591 | A | | 3/1999 | Powell et al. |
| 5,902,259 | A | * | 5/1999 | Wilkerson .................... 602/27 |
| 5,921,947 | A | * | 7/1999 | Kessler ......................... 602/27 |
| 6,117,098 | A | * | 9/2000 | Weber et al. .................. 602/27 |
| 6,267,742 | B1 | * | 7/2001 | Krivosha et al. .............. 602/28 |

* cited by examiner

Primary Examiner—Nicholas D. Lucchesi
Assistant Examiner—Huong Q. Pham
(74) Attorney, Agent, or Firm—Caesar, Rivise, Bernstein, Cohen & Pokotilow, Ltd.

(57) ABSTRACT

An ankle brace having a lateral upright limb member and a medial upright limb member to which a footplate/stirrup is pivotably secured. The brace includes a medial sling mechanism including a medial lifting strap secured to the stirrup at the location of the medial arch and arranged to be extended over the wearer's foot for releasable connection to the lateral upright. A lateral sling mechanism is also provided. The lateral sling mechanism includes a lateral lifting strap secured to the stirrup at the location of the lateral arch and slightly posteriorly of the medial sling strap. The lateral lifting strap is arranged to be extended over the wearer's foot to releasable connection to the medial upright. The footplate/stirrup includes a pair or recesses into which portions of respective ones of the lifting straps extend and a cushion pad covering the recesses.

28 Claims, 6 Drawing Sheets

ANKLE BRACE WITH ARCH SLING SUPPORT

FIELD OF THE INVENTION

This invention relates generally to ankle braces and more particularly to ankle braces for applying a lifting force to selected portions of the foot.

BACKGROUND OF THE INVENTION

Various ankle braces or supports have been disclosed in the patent literature for applying a lifting force to one or more portion of the foot for various reasons. Examples of such prior art patents are: U.S. Pat. Nos.: 4,494,534 (Hutson); 4,523,394 (Lindh et al.); 4,587,962 (Greene et al.); 4,753,229 (Sutherland); 5,016,623 (Krahenbuhl); 5,069,202 (Prock); 5,496,263 (Fuller II, et al.); 5,741,222 (Fiore); and 5,887,591 (Powell et al.).

It is well recognized among experts in podiatric and lower extremity biomechanics that the critical pivotal joint of the human foot is the talo-navicular joint. Previously, most foot orthotic interventions were designed to control the subtalar joint. Attempts to control the talo-navicular joint (medial flange, sustentaculum support) have caused potential irritation to this sensitive part of the human foot. Yet, recent experimental evidence, using arthrodesis procedures of cadaver models, have clearly shown that control of the talo-navicular joint will have profound control and limitation of the entire rearfoot complex, including the subtalar and calcaneal-cuboid joints.

To control the talo-navicular joint, a force, or moment must be applied medial to the axis of the entire rearfoot complex, which is slightly deviated in a more vertical alignment to the subtalar joint axis. To prevent plantar and medial migration of the head of the talus, the force must be applied in a dorsal, posterior and lateral direction which would cross almost perpendicular to the axis of rotation of the rearfoot complex. Heretofore no ankle brace has achieved that end.

In particular, the spring ligament complex of the human foot is the only structure that is anatomically designed to provide precise support of the talo-navicular joint. In severe foot pathologies such as the adult acquired flatfoot secondary to posterior tibial tendon dysfunction, the spring ligament complex becomes attenuated and the resultant foot deformity is uncontrolled with standard foot orthoses. Prior art in-shoe foot orthoses cannot apply significant moment of force in the proper direction to adequately control the talo-navicular joint.

SUMMARY OF THE INVENTION

This invention relates to an ankle brace comprising a stirrup or foot support, a lateral side limb member, a medial side limb member, and at least one lifting strap. The lateral side limb member is arranged for securement to the lateral side of a wearer's leg. The medial side limb member is arranged for securement to the medial side of the wearer's leg. The stirrup is arranged to receive the foot of the wearer and comprises a bottom plate having heel receiving end, a medial side, a contiguous medial arch area, a lateral side, a contiguous lateral arch area, a lateral sidewall projecting upward from the bottom plate on the lateral side adjacent the heel receiving end, and a medial sidewall projecting upward from the bottom plate on the medial side adjacent the heel receiving end. The lateral sidewall is pivotably connected to the lateral side limb member. The medial sidewall is pivotably connected to the medial side limb member.

In accordance with one aspect of this invention, the at least one lifting strap is a medial lifting strap that includes a first portion secured to the bottom plate at the arch area and projecting upward from the medial side of the bottom plate for extension over the foot of the wearer. The medial lifting strap also includes a second portion arranged for releasable securement to the lateral side limb member, whereupon when the second portion of the medial lifting strap is secured to the lateral side limb member the medial lifting strap applies a lifting force to the foot crossing perpendicularly to the axis of rotation of the foot's subtalar joint and the foot's rear foot complex joints.

In accordance with another aspect of this invention, the at least one lifting strap is a lateral lifting strap that includes a first portion secured to the bottom plate adjacent the lateral arch area and projecting upward from the lateral side of the bottom plate for extension over the foot of the wearer. The lateral lifting strap also includes a second portion arranged for releasable securement to the medial side limb member, whereupon when the second portion of the lateral lifting strap is secured to the medial side limb member the lateral lifting strap applies a lifting force to elevate the lateral longitudinal arch.

In accordance with still another aspect of this invention, the brace includes a first lifting strap and a lifting second strap. The first lifting strap is a medial lifting strap that includes a first portion secured to the bottom plate at the arch area and projecting upward from the medial side of the bottom plate for extension over the foot of the wearer. The medial lifting strap also includes a second portion arranged for releasable securement to the lateral side limb member, whereupon when the second portion of the medial lifting strap is secured to the lateral side limb member the medial lifting strap applies a lifting force to the foot crossing perpendicularly to the axis of rotation of the foot's subtalar joint and the foot's rear foot complex joints. The second lifting strap is a lateral lifting strap that includes a first portion secured to the bottom plate adjacent the lateral arch area and projecting upward from the lateral side of the bottom plate for extension over the foot of the wearer. The lateral lifting strap also includes a second portion arranged for releasable securement to the medial side limb member, whereupon when the second portion of the lateral lifting strap is secured to the medial side limb member the lateral lifting strap applies a lifting force to the foot to elevate the lateral longitudinal arch.

In accordance with another aspect of this invention the bottom plate of the ankle brace includes a medial recess located at the medial side in the arch area and/or a lateral recess located at the lateral side in the vicinity of the calcaneal cuboid joint area of the lateral arch. With respect to the medial recess a portion the first portion of the medial lifting strap is arranged to be located within the medial recess to apply the lifting force to the talo-navicular joint of the wearer's foot. With respect to the lateral recess a portion the first portion of the lateral lifting strap is arranged to be located within the lateral recess to apply the lifting force to elevate the lateral longitudinal arch.

DETAILED DESCRIPTION OF THE PREFERRED EMBODIMENT

Figure 1:
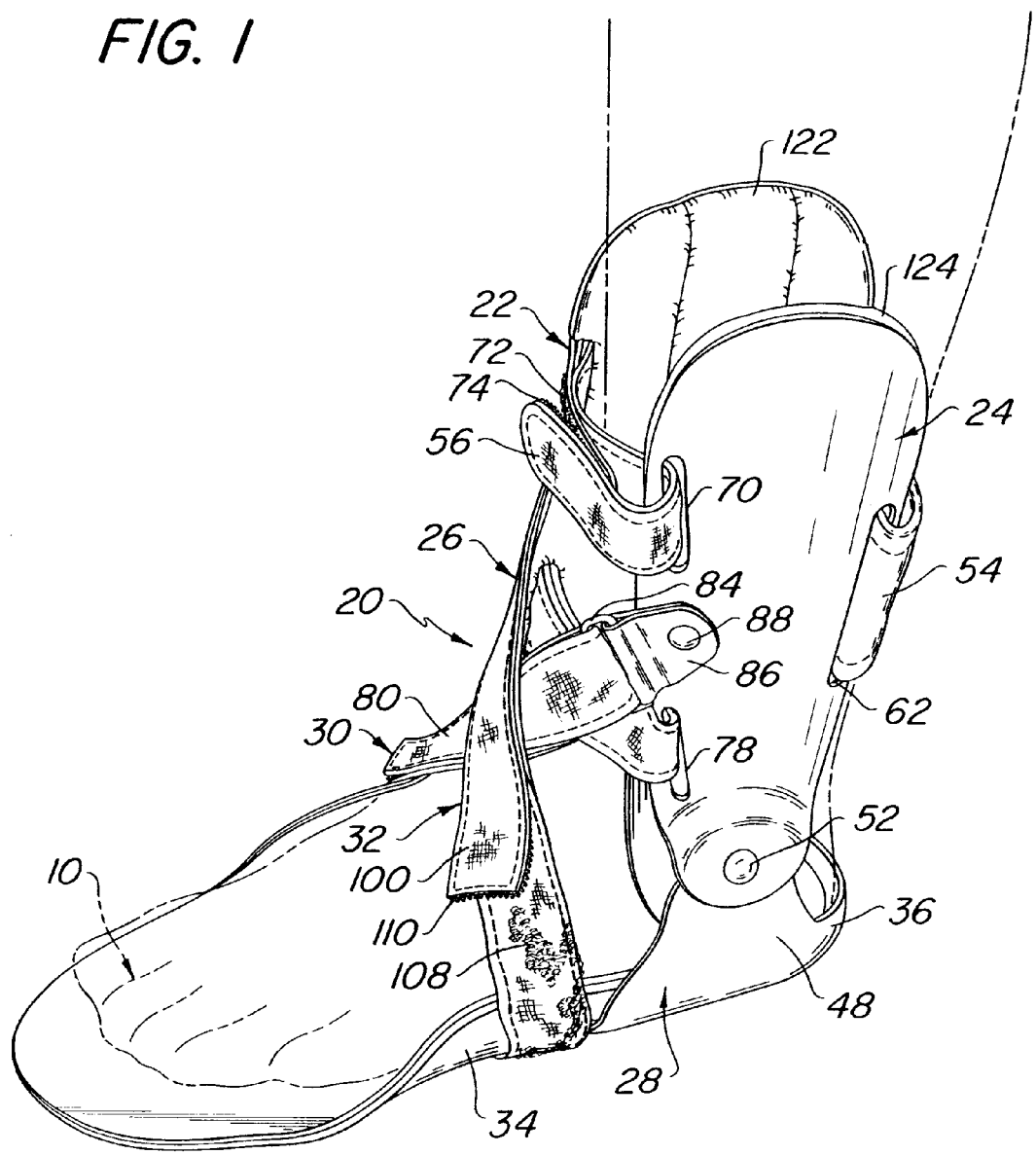
FIG. 1 is an isometric view, taken from the lateral side of the foot, showing one preferred exemplary embodiment of an ankle brace constructed in accordance with this invention having two lifting straps for selectively applying a lifting force to respective portions of the wearer's foot.

Referring now to the various figures of the drawing wherein like reference characters refer to like parts, there is shown in FIG. 1 one exemplary embodiment of an ankle brace 20 constructed in accordance with this invention. As will be described in detail later the brace 20 basically comprises a pair of upright limb members 22 and 24 for securement to the medial and lateral sides, respectively, of the leg of the wearer via an attachment strap system 26. The brace also includes a foot support or stirrup 28 that is arranged to receive the foot of the wearer and is pivotally connected to the limb members, and two "arch sling" mechanisms 30 and 32 connected to the stirrup and arranged to be coupled to the limb members 24 and 22, respectively, as will be described later. The arch sling mechanism 30 is referred to as a "medial" arch sling mechanism, while the arch sling mechanism 32 is referred to as a "lateral" arch sling mechanism."

The support stirrup 28 is a semi-rigid member formed, e.g., molded as an integral unit, of any suitable plastic material and is shaped to accommodate the foot 10 of the wearer. The stirrup or footplate may be a custom orthotic footplate or may be of a more universal shape. The stirrup 28 is arranged to be placed directly under the talo-navicular joint of the foot 10 as dictated by markings on an impression cast (not shown) of the wearer's foot, taken by the prescribing practitioner. The stirrup 28 includes a bottom plate 34 (FIG. 3) having heel receiving end 36, a medial side 38, a contiguous medial arch area 40, a lateral side 42, a contiguous lateral arch area 44. A medial sidewall 46 (FIGS. 2 and 7) projects upward from the bottom plate 34 on the medial side 38 adjacent the heel receiving end 36. In a similar manner a lateral sidewall 48 projects upward from the bottom plate 34 on said lateral side adjacent the heel receiving end 36. The medial sidewall 46 is pivotably connected to the lower end of the medial side limb member 22 by a metal rivet 50. The lateral sidewall 48 is similarly connected to the lower end of the lateral side limb member 24 by a metal rivet 52. Accordingly, the stirrup 28 is enabled to pivot about the respective axes of the rivets 50 and 52 to enable the wearer's foot to articulate normally when wearing the brace 20.

Figure 2:
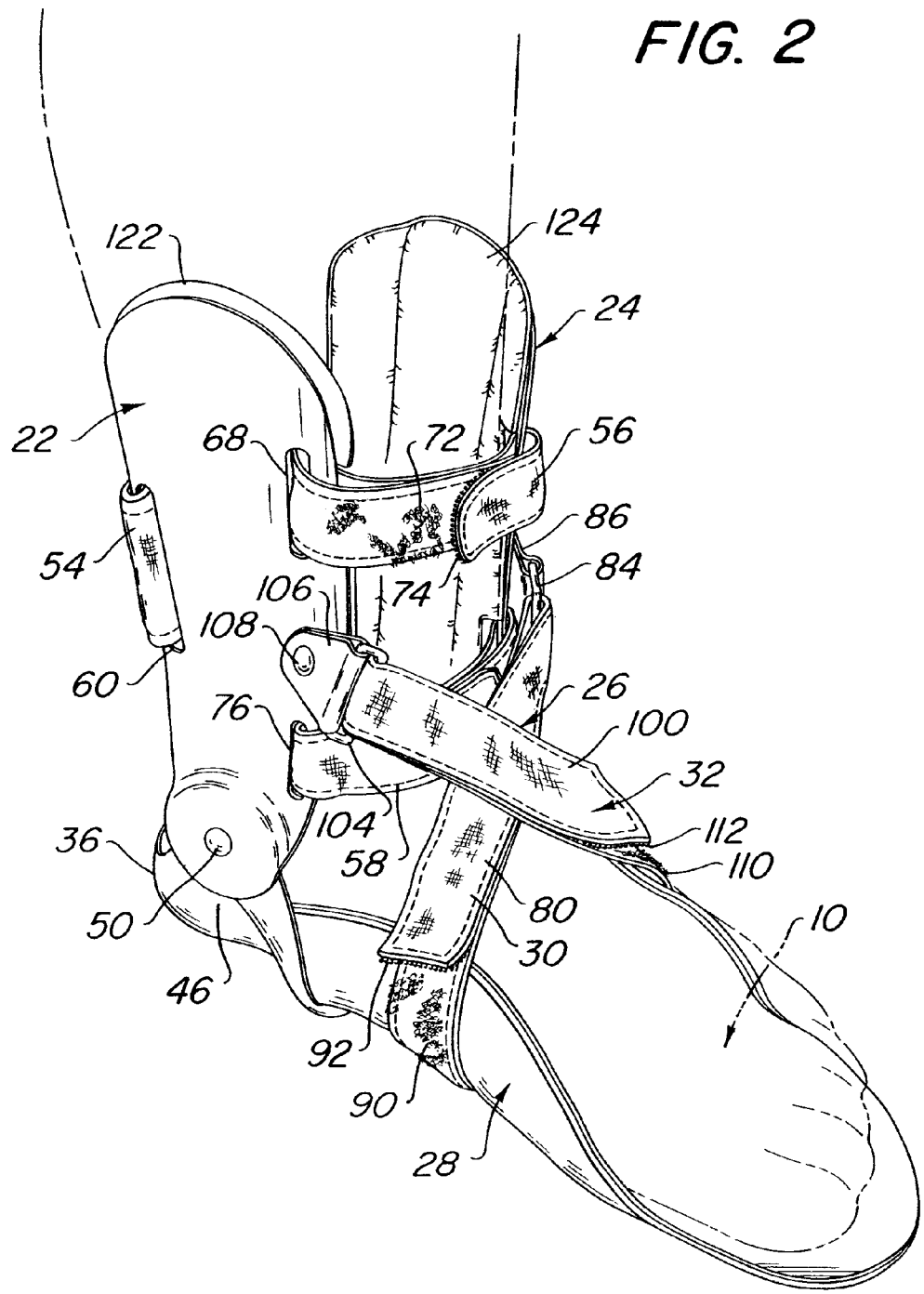
FIG. 2 is an isometric view of the ankle brace of FIG. 1, but taken from the medial side of the foot of the wearer.

As best seen in FIGS. 1 and 2 the medial side limb member 22 is an elongated member shaped to accommodate the medial side of the lower leg of the wearer and is preferably molded, formed, e.g., of the same material as the stirrup 28. In a similar manner the lateral side limb member 24 is an elongated member shaped to accommodate the lateral side of the lower leg of the wearer and is also preferably formed, e.g., molded, of the same material as the stirrup 28. In order to secure the side limb members 22 and 24 onto the leg of the wearer plural mounting straps 54, 56 and 58 are provided. In particular, the strap 54 serves to secure the posterior of the medial and lateral side limb members 22 and 24, respectively, on the posterior of the wearer's leg. The strap 56 serves to secure the top of medial and lateral side limb members on the anterior of the wearer's leg, while the strap 58 serves to secure the bottom of the of those members on the anterior of the wearer's leg.

The posterior mounting strap 54 is a relatively wide strap 54 of a flexible material, e.g., nylon, that is arranged to be formed into a loop and extended through a longitudinally extending slots 60 and 62 in the medial and lateral limb members 22 and 24, respectively. The slot 60 (FIG. 2) is located closely adjacent the posterior edge of the medial limb member 22 and at approximately the midpoint of the length of that member. The slot 62 (FIG. 1) is located closely adjacent the posterior edge of the lateral limb member 24 and at approximately the midpoint of the length of that member. The strap 54 includes a strip 64 (FIGS. 4–6) of a multi-loop component of a Velcro® fastening system secured, e.g., sewn, on the outer surface of the strap 54 adjacent one end thereof. A cooperating strip 66 (FIGS. 4–6) of a multi-hook component of that Velcro® fastening system is secured, e.g., sewn, on the inner surface of the strap 54 adjacent the other end thereof. The strips 64 and 66 are arranged to be brought into releasable engagement with each other to secure the strap in place and to adjust the tightness of the limb members 22 and 24 on the posterior of the leg of the wearer.

The upper anterior mounting strap 56 is narrower than the relatively wide posterior mounting strap 54 and is also formed of a flexible material, e.g., nylon, arranged to be formed into a loop and extended through a pair of slots 68 and 70 in the medial and lateral limb members, respectively. To that end, the medial limb member 22 includes a longitudinally extending slot 68 (FIG. 2) located closely adjacent to its anterior edge near the top of the member 22. The lateral limb member 24 includes a longitudinally extending slot 70 (FIG. 1) located closely adjacent to its anterior edge near the top of the member 24. The strap 56 is arranged to be formed into a loop and extended through the longitudinally extending slots 68 and 70 in the medial and lateral limb members 22 and 24, respectively. To that end the strap 56 includes a strip 72 (FIG. 1) of a multi-loop component of a Velcro® fastening system secured, e.g., sewn, on the outer surface of the strap 56 adjacent one end thereof. A cooperating strip 74 (FIG. 1) of a multi-hook component of that Velcro® fastening system is secured, e.g., sewn, on the inner surface of the strap 56 adjacent the other end thereof. The strips 72 and 74 are arranged to be brought into releasable engagement with each other to secure the strap 56 in place and to adjust the tightness of the upper end of the limb members 22 and 24 on the anterior of the leg of the wearer.

The lower anterior mounting strap 58 is the same width and construction as the upper anterior mounting strap 56 and is also arranged to be formed into a loop and extended through a pair of slots 76 and 78 in the medial and lateral limb members, respectively. To that end the medial limb member 22 includes a longitudinally extending slot 76 (FIG. 2) located closely adjacent its anterior edge near its bottom. The lateral limb member 24 includes a longitudinally extending slot 78 (FIG. 1) located closely adjacent its anterior edge near its bottom. The strap 58 includes a strip 72 (not shown) of a multi-loop component of a Velcro® fastening system secured, e.g., sewn, on the outer surface of the strap 58 adjacent one end thereof. A cooperating strip 74 (FIG. 7) of a multi-hook component of that Velcro® fastening system is secured, e.g., sewn, on the inner surface of the strap 58 adjacent the other end thereof. The strips 72 and 74 of the strap 58 are arranged to be brought into releasable engagement with each other to secure the strap in place and to adjust the tightness of the lower end of the limb members 22 and 24 on the anterior of the leg of the wearer.

Once the wearer's foot 10 is located on the stirrup 28 and the medial and lateral limb members 22 and 24, respectively, are secured in place by the mounting straps 54, 56 and 58, the adjustment of the brace can be accomplished to effect the lifting of selected portions of the wearer's foot on the stirrup. In particular, the stirrup 28 is arranged to be pulled and secured in a dorsal, posterior and lateral direction by the wearer using the medial arch sling mechanism 30. In addition the stirrup is arranged to be pulled and secured a dorsal, posterior and medial direction by the wearer using the lateral arch sling mechanism 32.

The medial arch sling mechanism 30 includes a strap 80 that is secured by a rivet 82 (FIG. 3) to the underside of the stirrup 28 in the medial arch area 40. As best seen in FIGS. 1, 2, 6 and 7 the strap 80 is adapted to be pulled from the medial side of the stirrup 28 in the dorsal, posterior and lateral direction across the top of the foot 10 and releasably, adjustably connected to an adjustment ring 84 located on the lateral limb upright member 24. In particular, the ring 84 is a generally rectangular shaped loop that is mounted on the lateral upright limb member 24 by a pivoting mount 86. The mount 86 is formed of a strip of plastic material that is extended through the interior of the ring 84 and folded in two and pivotably secured to the upright limb member 24 by a rivet 88. The strap 80 includes a free end portion having a strip 90 (FIG. 2) of a multi-loop component of a Velcro® fastening system secured, e.g., sewn, on the outer surface of the strap 80 adjacent the free end of the strap. A cooperating strip 92 (FIG. 2) of a multi-hook component of that Velcro® fastening system is secured, e.g., sewn, on the inner surface of the strap 80 at the free end. The strap 80 when pulled in the proximal direction, as discussed above, is extended through the interior of the ring 84 and then the free end of the strap 80 is folded back over itself so that the strips 90 and 92 are brought into releasable engagement with each other to secure the strap in place. This action adjusts the amount of lift provided by the medial arch sling mechanism.

Figure 3:
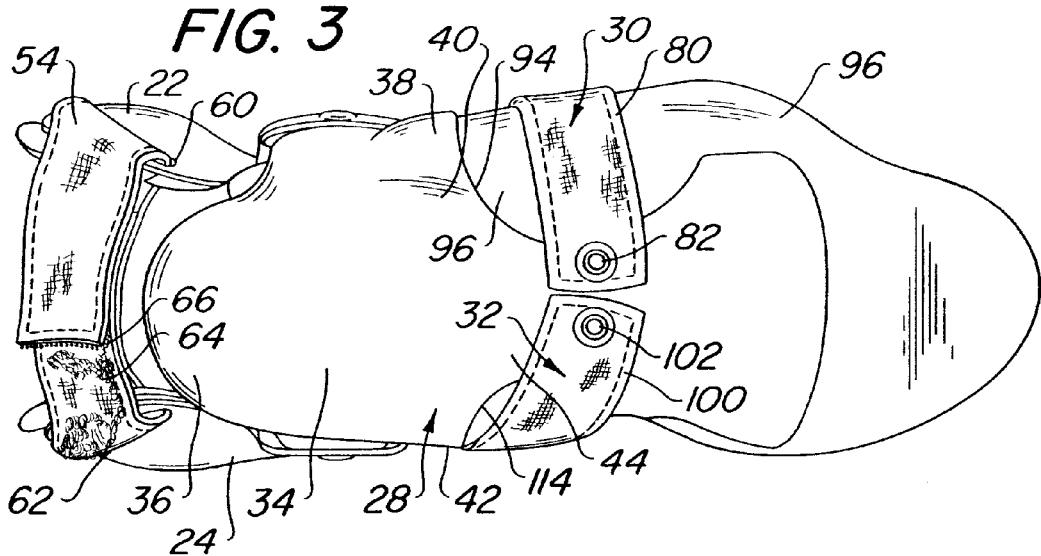
FIG. 3 is a plan view of the bottom of the ankle brace of FIGS. 1 and 2.
Figure 4:
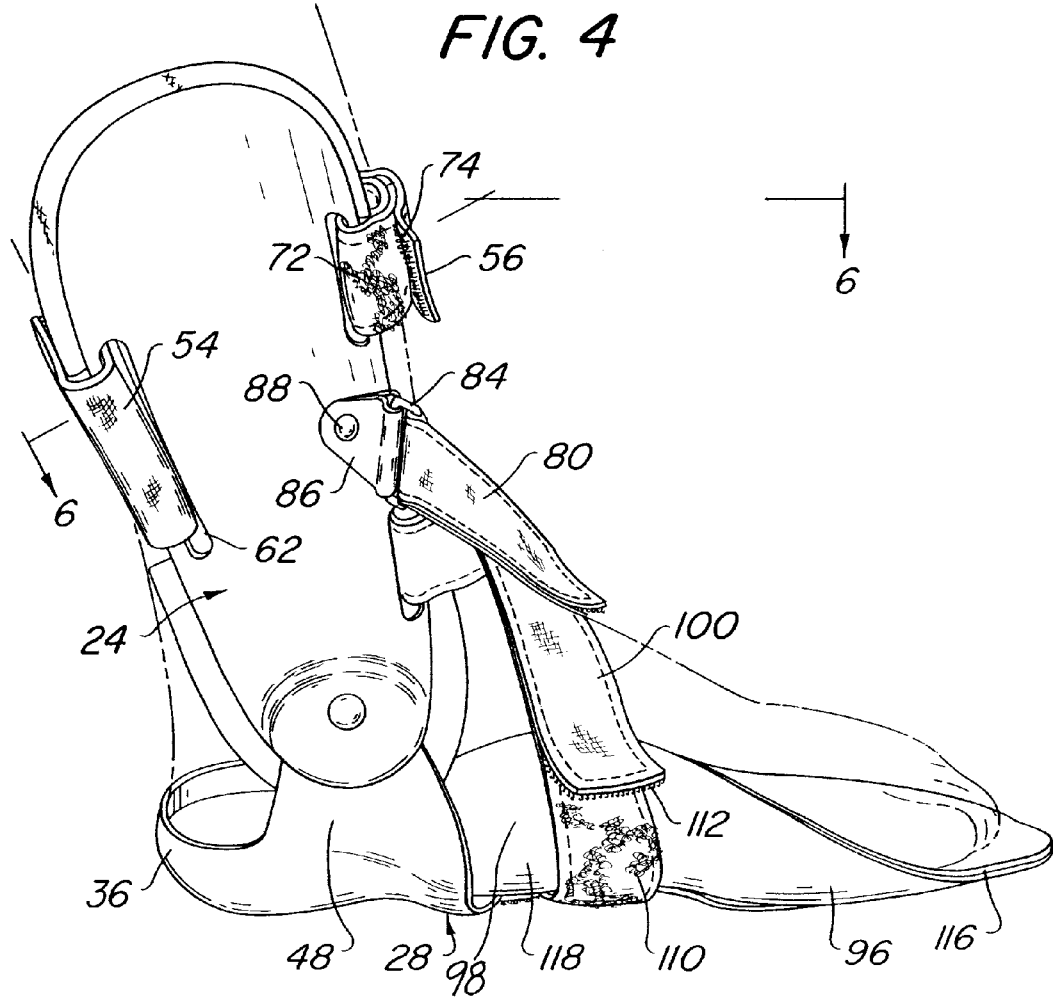
FIG. 4 is a medial side elevation view of the ankle brace of FIGS. 1 and 2.
Figure 5:
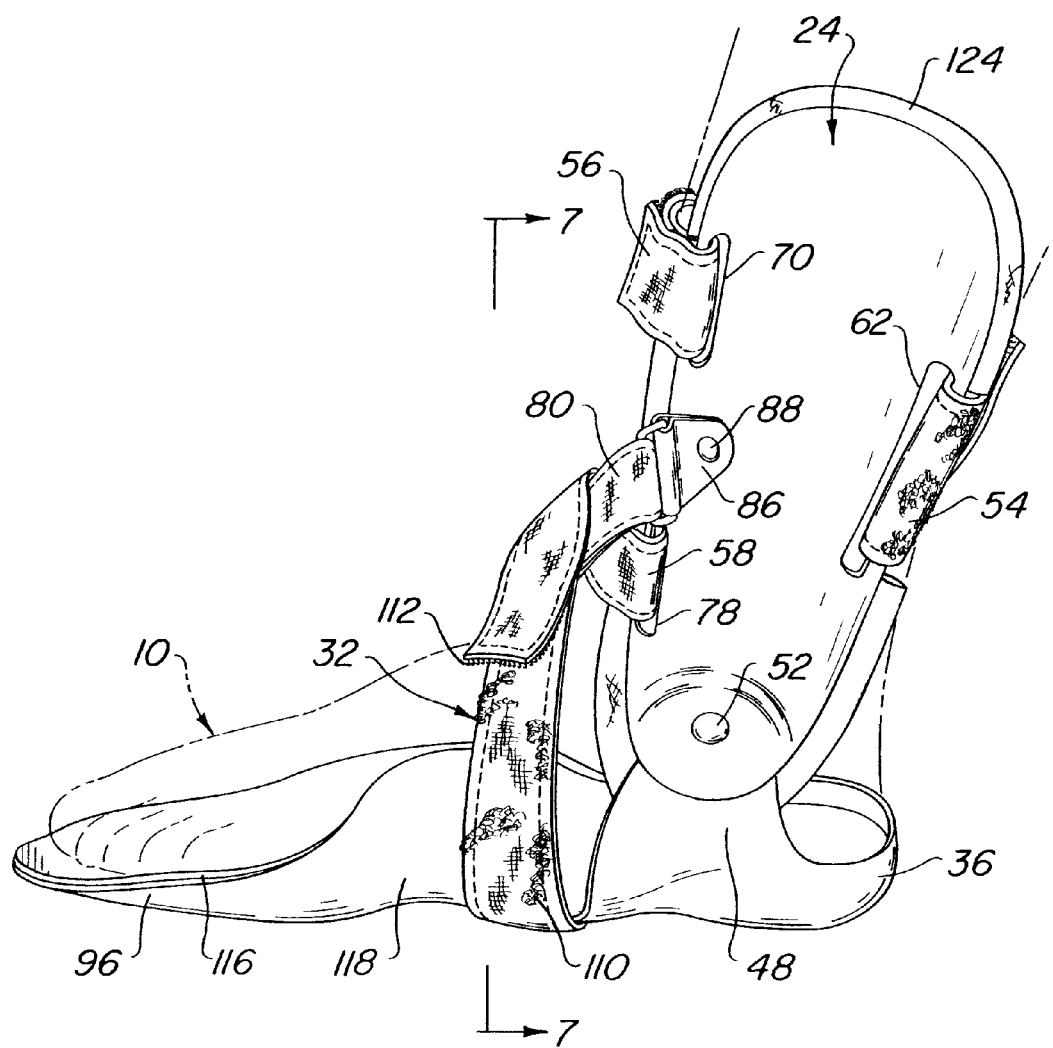
FIG. 5 is a lateral side elevation view of the ankle brace of FIGS. 1 and 2.
Figure 6:
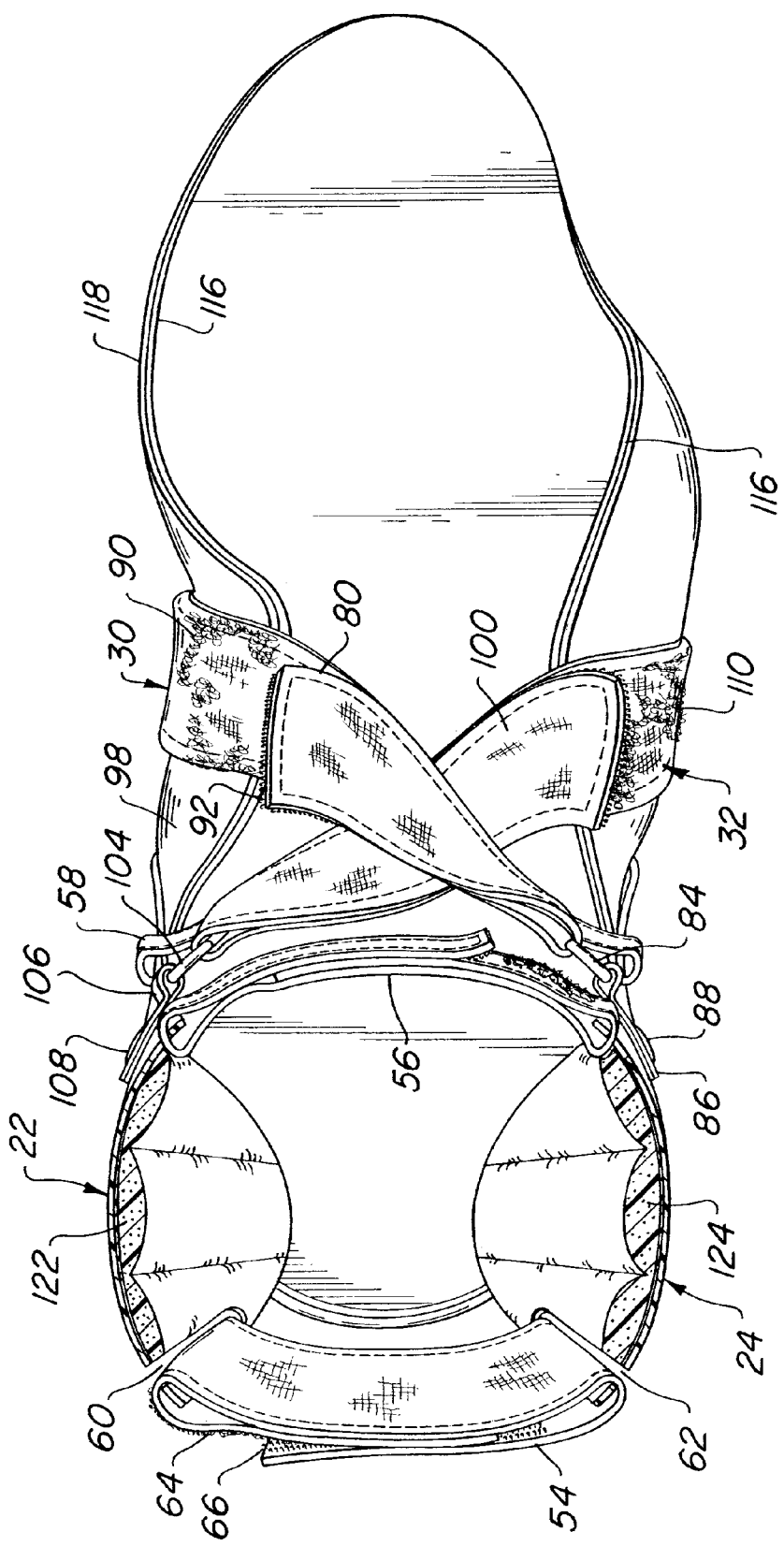
FIG. 6 is a sectional view taken along line 6—6 of FIG. 4.
Figure 7:
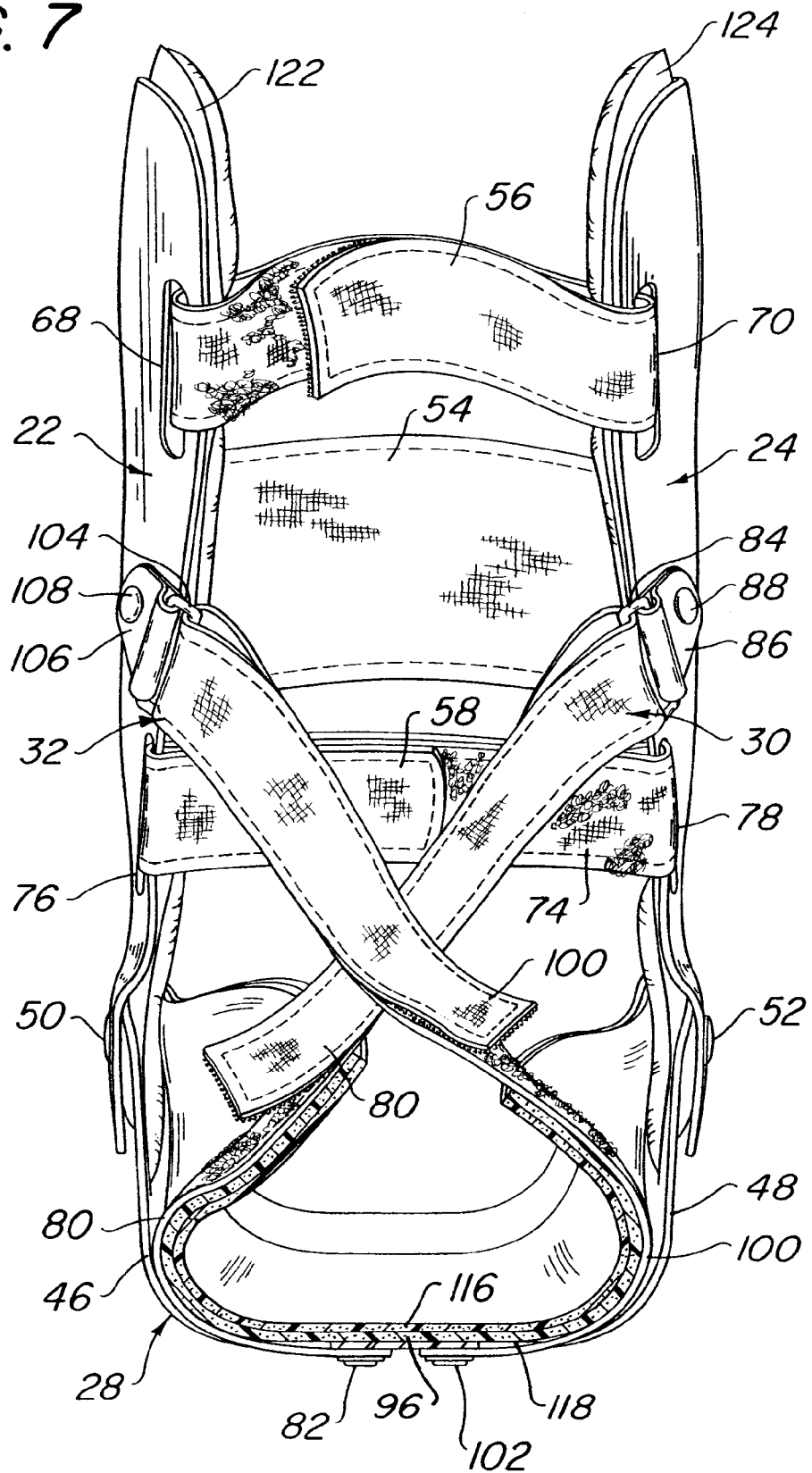
FIG. 7 is a sectional view taken along line 7—7 of FIG. 5.

As best seen in FIG. 3 a recess 94 is provided in the medial side of the stirrup 28 in the medial arch area, with a portion of the medial lifting strap 80 being arranged to reside in this recess when the medial lifting strap is secured to ring 84 on the lateral limb upright member 24. A cushion or pad 96 is located on the inside surface of the stirrup 28. The pad 96 covers the entire inner surface of the stirrup and extends beyond the front of the stirrup to accommodate the toes of the wearer as best seen in FIGS. 1, 2 and 4. The pad 96 includes a bulbous medial portion 98 (FIG. 4) that projects into (covers) the medial recess 96 of the stirrup 28 and extends substantially beyond the medial side of the stirrup to cushion the foot 10 from the lifting force provided by the strap 80 of the medial arch sling mechanism 30 when that strap is secured to the ring 84 on the lateral limb member 24. The pad 96 can be constructed of any suitable resilient or cushiony material, in a single layer or ply or multiple layers or plies of the same or different materials. In the embodiment shown the pad 96 includes an inner or upper layer or ply 116 and an outer or lower layer or ply 118 (FIGS. 6 and 7).

As should be appreciated by those skilled in the art from the foregoing the medial arch sling mechanism 30 serves to provide support to the talo-navicular joint of the wearer's foot 10. As is known, this is the central, key joint of the medial arch of the human foot. Unlike a typical arch support or foot orthotic of the prior art, the medial arch sling 30 mechanism of this invention provides a harness type mechanism to lift, align, reposition and support the medial arch and the talo-navicular joint of the human foot. Moreover, by virtue of the fact that the mechanism's strap 80 is arranged to be releasably and adjustably connected to the adjustment ring 84, the wearer can adjust the tension, e.g., the amount of lift, provided by the medial lifting strap 80 of the arch sling mechanism 30, at the talo-navicular joint. Further still, the adjustability of the connection between the strap 80 and the adjustment ring 84 enables the wearer to correct or adjust the amount of lift or tension as he/she ambulates and to adapt to the support over a period of minutes or hours. Thus, the medial arch sling mechanism 30 provides the wearer with the ability to implement and adjust the support of the critical area of his/her arch to achieve a new level of comfort and control not possible with standard foot orthoses or ankle foot orthoses. These advantages are achieved by the strap 80 of the medial arch sling mechanism 30 providing an adjustable lifting force in a superior-lateral direction to the medial arch of the human foot. The strap 80 is attached to the stirrup 28, e.g., an orthotic footplate, on the undersurface, lateral to the talo-navicular joint approximately centrally located in the middle of the stirrup/footplate. The strap 80 is directed medially towards the mid-arch. Here, the stirrup/footplate is cut or notched at 94 directly under the talo-navicular joint, to expose the foot of wearer at the talo-navicular joint. The foot is preferably uncovered by the plastic footplate to allow intimate contact of the strap 80 against the talo-navicular joint (medial arch area) of the foot of the wearer. Interposed between the lifting strap 80 of the sling mechanism 30, and the foot of the wearer, is the pad 96 which is affixed to the top surface of the stirrup/footplate. The pad serves to cushion the talo-navicular joint and disperse the lifting force evenly along the medial arch. The lifting strap 80 passes under the pad, beneath the talo-navicular joint of the medial arch, then is directed up the side of the medial arch, and across the top of the foot. At this point, the strap is directed superior and lateral, above the top of the foot and across to the fibular (lateral) limb support upright member 24 of the ankle brace. Thus, the strap 80 contacts the pad 96 placed under and at the medial side of the foot of the wearer. After coming up the medial side of the foot, the strap 80 no longer contacts the pad or the foot as it passes across the front of the ankle joint. The strap 80 is directed in a superior-lateral direction, passing obliquely across the front of the ankle joint, attaching to the mounting ring 84 at the mid-portion of the lateral limb upright, approximately five inches above the ankle joint line. The strap includes adjustable releasably securable components, e.g., Velcro® components, that allows the strap to be secured upon itself after passing through the ring, or could be redirected into a pre-cut notch (not shown) in the limb upright of the ankle brace.

The direction of pull of the lifting strap 80 is intentionally designed to cross perpendicular to the axis of rotation of the subtalar joint and the rearfoot complex joints. Application of this force perpendicular to the joint axis allows maximum leverage and efficiency in controlling or limiting movement of the bone segments on each side of the joint axis. The subtalar joint axis, from documented experimental scientific research, passes from inferior-proximal to superior-distal in a 45 degree inclination angulation from the supportive surface, beginning at the bottom of the heel bone (calcaneus) and exiting through the top of the midfoot dorsally. The arch sling strap 80 passes from the bottom of the midfoot, and angles 45 degrees from the supportive surface, and is directed from inferior-distal to superior-proximal (exactly the opposite direction as the subtalar joint axis) direction. The medial arch sling mechanism 30 is attached both above and below the axis of the subtalar joint, thus providing a force on both sides of the center of rotation of that joint. Most foot orthotics function to provide a force only to one side of the axis of joint rotation. Thus, the medial arch sling provides a powerful correction to the key joints of the human foot, i.e., the subtalar and talo-navicular joints, while providing support, and without sacrificing comfort.

As should also be appreciated by those skilled in the art from the foregoing the use of the medial arch sling mechanism 30 can be used for a variety of clinical indications to provide beneficial effects. Exemplary indications are: "AdultAcquired Flatfoot (Post. Tibial Tendon Dysfunction)," "Degenerative Arthritis of the Rearfoot," "Charcot Foot with Rocker-Bottom," "Tarsal Coalition," and "Degenerative Arthritis of Lisfranc's Joint."

For other indications, such as, "Lateral Ankle Instability," chronic tendon pathologies of the lateral foot and ankle ("Proneal Tendinopathy"), "Cuboid Subluxation Syndrome," recurrent stress fractures of the fifth metatarsal, "Sinus Tarsi Syndrome" or significant varus alignment deformities of the rearfoot complex, the use of the lateral arch sling mechanism 32 is desirable. To that end, as mentioned earlier, the exemplary embodiment of the brace 20 of this invention also includes a lateral arch sling mechanism 32. The lateral arch sling mechanism 32 is constructed in a similar manner to the medial arch sling mechanism 30. In particular, the lateral arch sling mechanism 32 includes a lateral strap 100 that is secured by a rivet 102 (FIG. 3) to the underside of the stirrup 28 in the lateral arch area 44 at a location opposite to connection point of the medial lifting strap 80 and slightly posteriorly.

As best seen in FIGS. 1, 2, 6 and 7 the lateral lifting strap 100 is adapted to be pulled from the lateral side of the stirrup/footplate 28 in the dorsal, posterior and medial direction across the top of the foot 10 and releasably, adjustably connected to an adjustment ring 104 located on the medial limb upright member 22. In particular, the ring 104 is a generally rectangular shaped loop that is mounted on the medial upright limb member 22 by a pivoting mount 106. The mount 106 is formed like the mount 86 and is secured to the upright limb member by a rivet 108. The strap 100 of the lateral lift mechanism 32 includes a free end portion having a strip 110 (FIGS. 2 and 4) of a multi-loop component of a Velcro® fastening system secured, e.g., sewn, on the outer surface of the strap 100 adjacent the free end thereof. A cooperating strip 112 of a multi-hook component of that Velcro® fastening system is secured, e.g., sewn, on the inner surface of the strap 100 at the free end. The strap 100 is arranged to be pulled in the dorsal, posterior and medial direction and extended through the interior of the ring 104 and then the free end of the strap 100 is folded back over itself so that the strips 110 and 112 are brought into releasable engagement with each other to secure the strap in place. This action adjusts the amount of lift provided by the lateral arch sling mechanism.

As best seen in FIG. 3 a recess 114 is provided in the lateral side of the stirrup 28 in the vicinity of the calcaneal cuboid joint area of the lateral arch area 34. A portion of the lateral lifting strap 100 of the lateral sling mechanism 32 is arranged to reside in the recess 114 when the strap 100 is secured to ring 104 on the medial limb upright member 24. The stirrup cushion 96 also includes a bulbous lateral portion 116 (FIGS. 4 and 5) that projects into and covers the lateral recess 114 of the stirrup 28 and extends beyond the lateral side of the stirrup to cushion the foot 10 from the lifting force provided by the strap 100 of the lateral arch sling mechanism 32. When the strap 100 of the lateral arch sling mechanism 32 is pulled from the lateral side of the stirrup in the dorsal, posterior and medial direction across the top of the foot and releasably, adjustably connected to an adjustment ring 104 located on the medial limb upright member 24 the strap courses laterally underneath the lateral recess 114 then superiorly and medially to the adjustment ring 104. By tightening the strap 100 the user is able to elevate his/her lateral longitudinal arch to a degree desired.

In the interest of wearer comfort each of the upright limb members 22 and 24 includes a respective pad releasably mounted therein. In particular, a cushion or pad 122 having the same peripheral shape, but slightly larger, as the medial upright limb member 22 is arranged to be releasably secured to the inner surface of that limb member. The pad 122 includes slots or notches located at the location of the slots in the limb member 22 to enable the mounting straps 54, 56 and 58 to be extended therethrough without interference. The releasable securement of the pad 122 on the inner surface of the upright limb member 22 is accomplished by the use of respective patches (not shown) of a multiloop component of a Velcro® fastening system secured, e.g., glued, on the inner surface of the upright limb member 22. A cooperating patch (not shown) of a multi-hook component of that Velcro® fastening system is secured, e.g., glued, on the inner surface of the pad 122. The Velcro® patches are arranged to be brought into releasable engagement with each other to secure the pad in place. The lateral upright member 24 includes a similarly constructed cushion or pad 124 releasably secured thereto in the same manner as the pad 122 of the upright member 22.

As mentioned earlier the brace 20 is merely exemplary of various braces that can be constructed in accordance with this invention. Thus a brace may be constructed to include only the medial sling mechanism or only the lateral sling mechanism, and not both. Moreover, the construction of the uprights 22 and 24 need not be of the type shown. So too, the stirrup's pad may be constructed differently than that shown and described above. Other variations are also contemplated. For example, the stirrup/footplate need not have a specific notch type cutout, but, rather, could be cut narrow along its entire medial length to allow contact of the lifting strap. Moreover, in the case of a medial lifting strap, that strap need not be attached to the undersurface of the footplate. Instead, a padded cover, or flap of material extending from the top surface of the footplate, could extend under the talo-navicular joint area, up medially along the side of the foot, and then serve as an attachment for the strap which would continue on as previously described. The padded cover, could be constructed so that it provides some stretch type forgiveness, to provide an elastic type support under the talo-navicular area, rather than the firmness of the strap itself. Moreover, as noted above, the stirrup/footplate could be either a custom or non-custom design. A custom footplate can be fabricated from a plaster model made of the user's foot. Both footplates have a contoured arch and are designed to control subtalar and midtarsal joint motion of the human foot. Non-custom footplates could be fabricated from models of average foot shapes and sizes.

A universal brace constructed in accordance with this invention makes use of the medial arch sling combined with the lateral arch sling. The combination of these two strap supports provides a variation of the popular "Figure Eight" shaped ankle brace configurations utilized by athletic trainers and physical therapists. The combination of a lateral and medial arch sling strap allows the application of a support to both the medial and lateral aspect of the foot and ankle. The foot is therefore protected from the medial ankle sprains and lateral ankle sprains. In addition, the use of both straps allows the custom positioning and support of the foot for adjustment and positioning inside of the athletic shoe. Based upon the patient's foot type, the user can tighten the medial and lateral straps to provide a customized positioning of the foot, perhaps overcorrecting medially or overcorrecting laterally, depending on the specific need of the patient. The unique benefits of the proposed double-strap arch sling mechanism is the fact that the straps themselves to not actually contact the ankle joint anteriorly or the leg anteriorly. Therefore, a "Figure Eight" support is provided to the athlete, yet, there is no inhibition of the natural sagittal plane movement of the ankle joint. Other traditional Figure Eight strap closures provide medial and lateral support but also, unfortunately, wrap around the anterior aspect of the ankle and inhibit natural ankle joint motion. Thus, the performance of the athlete can be compromised. Therefore, the benefits of the subject double strap arch sling mechanism is the accomplishment of significant medial and lateral support while preserving total natural sagittal plane (up and down) movement of the ankle joint.

Without further elaboration the foregoing will so fully illustrate my invention that others may, by applying current or future knowledge, adopt the same for use under various conditions of service.

I claim:

1. An ankle brace comprising a stirrup, a lateral side limb member, a medial side limb member, and a medial lifting strap, said lateral side limb member being arranged for securement to the lateral side of a wearer's leg, said medial side limb member being arranged for securement to the medial side of the wearer's leg, said stirrup being arranged to receive the foot of the wearer and comprising a bottom plate having heel receiving end, a medial side, a contiguous medial arch area, a lateral side, a contiguous lateral arch area, a lateral sidewall projecting upward from said bottom plate on said lateral side adjacent said heel receiving end, and a medial sidewall projecting upward from said bottom plate on said medial side adjacent said heel receiving end, said lateral sidewall being pivotably connected to said lateral side limb member, said medial sidewall being pivotably connected to said medial side limb member, said medial lifting strap including a first portion secured to said bottom plate at said medial arch area under the tarsal region of the arch of the wearer's foot and projecting upward from said medial side of said bottom plate for extension over the foot of the wearer, said medial lifting strap also including a second portion arranged for releasable securement to said lateral side limb member, whereupon when said second portion of said medial lifting strap is secured to said lateral side limb member said medial lifting strap applies a lifting force to the foot crossing perpendicularly to the axis of rotation of the foot's subtalar joint and the foot's rear foot complex joints.

2. The ankle brace of claim 1 wherein said bottom plate includes a recess located at said medial side in said medial arch area, a portion said first portion of said medial lifting strap being arranged to be located within said medial recess to apply said lifting force to the talo-navicular joint of the wearer's foot.

3. The ankle brace of claim 1 wherein the amount of lifting force provided by said medial lifting strap is adjustable.

4. The ankle brace of claim 3 additionally comprising a connector member mounted on said lateral side limb member for releasably engaging said second portion of said medial lifting strap at various positions therealong to adjust the amount of lifting force provided by said medial lifting strap.

5. The ankle brace of claim 4 wherein said connector member comprises a ring and wherein said second portion of said strap terminates in a free end having one component of a multi-hook and multi-loop fastening system and an adjacent cooperating component of said multi-hook and multi-loop fastening system, said free end being arranged to be extended through said ring and folded back over itself, whereupon said one component of said multi-hook and multi-loop fastening system releasably engages said other component of said multi-hook and multi-loop fastening system.

6. The ankle brace of claim 2 additionally comprising a pad affixed to said bottom plate and extending over said recess to disperse said lifting force provided by said medial lifting strap.

7. The ankle brace of claim 2 wherein said bottom plate has an undersurface and wherein said first portion of said strap is secured to said foot plate on said undersurface lateral to the talo-navicular joint approximately centrally located in the middle of the foot plate.

8. The ankle brace of claim 7 additionally comprising a pad affixed to said bottom plate and extending over said recess to disperse said lifting force provided by said medial lifting strap.

9. The ankle brace of claim 8 wherein said includes a medial side portion extending outward substantially beyond said medial side of said bottom plate for deployment over the contiguous portion of the wearer's foot.

10. An ankle brace comprising a stirrup, a lateral side limb member, a medial side limb member, and a lateral lifting strap, said lateral side limb member being arranged for securement to the lateral side of a wearer's leg, said medial side limb member being arranged for securement to the medial side of the wearer's leg, said stirrup being arranged to receive the foot of the wearer and comprising a bottom plate having heel receiving end, a medial side, a contiguous medial arch area, a lateral side, a contiguous lateral arch area, a lateral sidewall projecting upward from said bottom plate on said lateral side adjacent said heel receiving end, and a medial sidewall projecting upward from said bottom plate on said medial side adjacent said heel receiving end, said lateral sidewall being pivotably connected to said lateral side limb member, said medial sidewall being pivotably connected to said medial side limb member, said lateral lifting strap including a first portion secured to said bottom plate at said lateral arch area under the tarsal region of the arch of the wearer's foot and projecting upward from said lateral side of said bottom plate for extension over the foot of the wearer, said lateral lifting strap also including a second portion arranged for releasable securement to said medial side limb member, whereupon when said second portion of said lateral lifting strap is secured to said medial side limb member said lateral lifting strap applies a lifting force to the foot to elevate the lateral arch.

11. The ankle brace of claim 10 wherein said bottom plate includes a recess located at said lateral side in the vicinity of the calcaneal cuboid joint area of the lateral arch, a portion said first portion of said lateral lifting strap being arranged to be located within said lateral recess to apply said lifting force.

12. The ankle brace of claim 10 wherein the amount of lifting force provided by said lateral lifting strap is adjustable.

13. The ankle brace of claim 12 additionally comprising a connector member mounted on said medial side limb member for releasably engaging said second portion of said lateral lifting strap at various positions therealong to adjust the amount of lifting force provided by said lateral lifting strap.

14. The ankle brace of claim 13 wherein said connector member comprises a ring and wherein said second portion of said strap terminates in a free end having one component of a multi-hook and multi-loop fastening system and an adjacent cooperating component of said multi-hook and multi-loop fastening system, said free end being arranged to be extended through said ring and folded back over itself whereupon said one component of said multi-hook and multi-loop fastening system releasably engages said other component of said multi-hook and multi-loop fastening system.

15. The ankle brace of claim 11 additionally comprising a pad affixed to said bottom plate and extending over said lateral recess to disperse said lifting force provided by said lateral lifting strap.

16. The ankle brace of claim 11 wherein said bottom plate has an undersurface and wherein said first portion of said lateral lifting strap is secured to said bottom plate on said undersurface adjacent the calcaneal cuboid joint area of the lateral arch.

17. The ankle brace of claim 16 additionally comprising a pad affixed to said bottom plate and extending over said lateral recess to disperse said lifting force provided by said lateral lifting strap.

18. The ankle brace of claim 17 wherein said pad includes a medial side portion extending outward substantially beyond said lateral side of said bottom plate for deployment over the contiguous portion of the wearer's foot.

19. An ankle brace comprising a stirrup, a lateral side limb member, a medial side limb member, a medial lifting strap and a lateral lifting strap, said lateral side limb member being arranged for securement to the lateral side of a wearer's leg, said medial side limb member being arranged for securement to the medial side of the wearer's leg, said stirrup being arranged to receive the foot of the wearer and comprising a bottom plate having heel receiving end, a medial side, a contiguous medial arch area, a lateral side, a contiguous lateral arch area, a lateral sidewall projecting upward from said bottom plate on said lateral side adjacent said heel receiving end, and a medial sidewall projecting upward from said bottom plate on said medial side adjacent said heel receiving end, said lateral sidewall being pivotably connected to said lateral side limb member, said medial sidewall being pivotably connected to said medial side limb member, said medial lifting strap including a first portion secured to said bottom plate at said medial arch area under the tarsal region of the arch of the wearer's foot and projecting upward from said medial side of said bottom plate for extension over the foot of the wearer, said medial lifting strap also including a second portion arranged for releasable securement to said lateral side limb member, whereupon when said second portion of said medial lifting strap is secured to said lateral side limb member said medial lifting strap applies a lifting force to the foot crossing perpendicularly to the axis of rotation of the foot's subtalar joint and the foot's rear foot complex joints, said lateral lifting strap including a first portion secured to said bottom plate at said lateral arch area under the tarsal region of the arch of the wearer's foot and projecting upward from said lateral side of said bottom plate for extension over the foot of the wearer, said lateral lifting strap also including a second portion arranged for releasable securement to said medial side limb member, whereupon when said second portion of said lateral lifting strap is secured to said medial side limb member said lateral lifting strap applies a lifting force to the foot to elevate the lateral arch.

20. The ankle brace of claim 19 wherein said bottom plate includes a medial recess located at said medial side in said medial arch area, a portion said first portion of said medial lifting strap being arranged to be located within said medial recess to apply said lifting force to the talo-navicular joint of the wearer's foot.

21. The ankle brace of claim 19 wherein said bottom plate includes a lateral recess located at said lateral side in said lateral arch area, a portion said first portion of said lateral lifting strap being arranged to be located within said lateral recess to apply said lifting force to elevate the lateral arch.

22. The ankle brace of claim 20 wherein said bottom plate includes a lateral recess located at said lateral side in said lateral arch area, a portion said first portion of said lateral lifting strap being arranged to be located within said lateral recess to apply said lifting force to elevate the lateral arch.

23. The ankle brace of claim 19 wherein the amount of lifting force provided by said medial lifting strap is adjustable.

24. The ankle brace of claim 19 wherein the amount of lifting force provided by said lateral lifting strap is adjustable.

25. The ankle brace of claim 23 wherein the amount of lifting force provided by said lateral lifting strap is adjustable.

26. The ankle brace of claim 22 additionally comprising a pad affixed to said bottom plate and extending over said medial recess to disperse said lifting force provided by said medial lifting strap.

27. The ankle brace of claim 22 additionally comprising a pad affixed to said bottom plate and extending over said lateral recess to disperse said lifting force provided by said lateral lifting strap.

28. The ankle brace of claim 26 additionally comprising a pad affixed to said bottom plate and extending over said lateral recess to disperse said lifting force provided by said lateral lifting strap.

* * * * *